(12) United States Patent
Chakrabarti

(10) Patent No.: US 10,947,566 B1
(45) Date of Patent: Mar. 16, 2021

(54) HYDROGEN PEROXIDE PRODUCTION METHOD, SYSTEM, AND APPARATUS

(71) Applicant: Gaurab Chakrabarti, Houston, TX (US)

(72) Inventor: Gaurab Chakrabarti, Houston, TX (US)

(73) Assignee: SOLUGEN, INC.

( * ) Notice: Subject to any disclaimer, the term of this patent is extended or adjusted under 35 U.S.C. 154(b) by 214 days.

(21) Appl. No.: 15/862,684

(22) Filed: Jan. 5, 2018

Related U.S. Application Data

(62) Division of application No. 14/799,651, filed on Jul. 15, 2015, now Pat. No. 9,890,397.

(51) Int. Cl.
| | | |
|---|---|---|
| *B01D 61/00* | (2006.01) | |
| *C12P 7/00* | (2006.01) | |
| *B01D 69/02* | (2006.01) | |
| *B01D 69/04* | (2006.01) | |

(52) U.S. Cl.
CPC .............. *C12P 7/00* (2013.01); *B01D 61/00* (2013.01); *B01D 69/02* (2013.01); *B01D 69/04* (2013.01); *B01D 2325/34* (2013.01)

(58) Field of Classification Search
CPC ..... B01D 61/00; B01D 2325/34; B01D 69/02
See application file for complete search history.

(56) References Cited

U.S. PATENT DOCUMENTS

| | | | |
|---|---|---|---|
| 4,321,324 A * | 3/1982 | Maselli | .................. C07H 3/02 435/105 |
| 4,920,055 A | 4/1990 | Hoiberg et al. | |
| 5,712,259 A | 1/1998 | Birkmayer | |
| 6,274,114 B1 | 8/2001 | Ledon et al. | |
| 6,712,949 B2 | 3/2004 | Gopal | |
| 2014/0234202 A1 | 8/2014 | Vandenbussche et al. | |
| 2014/0377798 A1 | 12/2014 | Ertl et al. | |
| 2015/0030505 A1 * | 1/2015 | Bloomfield | .............. B01J 10/00 422/117 |

FOREIGN PATENT DOCUMENTS

CN 103708426 A 4/2014

OTHER PUBLICATIONS

Siegel et al. NAD(P)H:Quionone Oxidoreductase 1 (NQ01) in the Sensitivity and Resistance to Antitumor Quinones; Biochemistry and Pharmacology, vol. 83, No. 8, pp. 1-18. (Year: 2012).*
Deed, Terry, "The Manufacture of Hydrogen Peroxide", New Zealand <retrieved on Oct. 15, 2015 from the web at: http://nzic.org.nz/ChemProcesses/production/1E.pdf>.

* cited by examiner

*Primary Examiner* — Susan M Hanley
*Assistant Examiner* — Paul C Martin
(74) *Attorney, Agent, or Firm* — Law Office of Sam Sokhansanj PLLC

(57) ABSTRACT

A hydrogen peroxide production method, system, and apparatus is provided for producing large volumes of hydrogen peroxide having concentrations up to and excess of 80% in one continuous cycle. In one aspect, the hydrogen peroxide production system can include an aqueous solution comprised of an NQO1 enzyme, an NQO1 activated compound or molecule, and an NADH or NADPH cofactor for producing hydrogen peroxide, a production chamber having a semi-permeable membrane for receiving the aqueous solution. Here, the membrane can further include one or more molecular weight barriers configured to diffuse the produced hydrogen peroxide there through. The system can also include a collection chamber for receiving the produced hydrogen peroxide, and one or more pumps for circulating the aqueous solution having the hydrogen peroxide to the collection chamber and back to the production chamber.

8 Claims, 11 Drawing Sheets

HYDROGEN PEROXIDE PRODUCTION METHOD, SYSTEM, AND APPARATUS

CROSS-REFERENCE TO RELATED APPLICATION

This application is a division of U.S. Non-Provisional application Ser. No. 14/799,651 filed on Jul. 15, 2015, and issued on Feb. 13, 2018 as U.S. Pat. No. 9,890,397, which is incorporated herein by reference in its entirety.

BACKGROUND

This section is intended to introduce the reader to aspects of art that may be related to various aspects of the present disclosure described herein, which are described and/or claimed below. This discussion is believed to be helpful in providing the reader with background information to facilitate a better understanding of the various aspects of the present disclosure described herein. Accordingly, it should be understood that these statements are to be read in this light, and not as admissions of prior art.

Industrial synthesis of hydrogen peroxide is predominantly achieved by using the Riedel-Pfleiderer process originally disclosed in U.S. Pat. Nos. 2,158,525 and 2,215,883. This well-known large scale cyclic production process of hydrogen peroxide makes use of the autoxidation of a 2-alkylanthrahydroquinone compound to the corresponding 2-alkylanthraquinone which results in the formation of hydrogen peroxide. In particular, the hydrogen peroxide is typically produced using a cyclical anthraquinone process (AO-process) comprising the hydrogenation of anthraquinone working solution in a catalytic reactor and the oxidation of the hydrogenated anthraquinone working solution by air in a multi-stage packed bed or sieve plate tower while simultaneously producing hydrogen peroxide in the organic stream, with the consecutive extraction of the hydrogen peroxide from the anthraquinone working solution by water in a multistage counter-current extraction column process. The organic solvent of choice is typically a mixture of two types of solvents, one being a good solvent of the quinone derivative (usually a mixture of aromatic compounds) and the other being a good solvent of the hydroxyquinone derivative (usually a long chain alcohol or cyclic ester). In addition to the main AO-process steps, there may be other ancillary process steps involved, such as the separation of the hydrogenation catalyst from the working solution; the recovery and polish purification of the anthraquinone working solution, the accompanying solvents, their recycle to the hydrogenator, and the recovery, polish purification and stabilization of the hydrogen peroxide product.

Accordingly, the conventional AO-processes and respective production plants are complicated and require many and large installments of equipment, a number of competent staff for maintenance of the equipment and operation of the main and ancillary process steps, and special safeguards to handle the resulting hydrogen peroxide in its usually high concentrations of 40 percent, and further distilled to concentrations of 50 to 70 percent. Hence, much management attention and frequent maintenance is required. Although one might assume that the AO-process may be performed on small- to medium-scale so as to merely satisfy local demand, in the state of the art it is still deemed that such processes require the use of many pieces of equipment, much management attention, and frequent maintenance, and that they are difficult to scale down and difficult to make such processes profitable.

Hence, what is needed is a method and system for producing hydrogen peroxide without the large capital costs associated with current large-scale to mega-scale production highly complex plants, and to develop a new process that would allow effective hydrogen peroxide production in portable and mobile units and small to medium size hydrogen peroxide production plant environments. In addition, the new process should be relatively simple to set-up, operate, start-up, or shut-down by an operator of any experience level without the need for high level technical training.

BRIEF SUMMARY

One or more aspects of the present disclosure described herein overcome the above shortfalls of prior attempted methods, devices, and systems. In particular, in one aspect of the present disclosure described herein, a hydrogen peroxide production method, system, and apparatus is provided for producing large volumes of hydrogen peroxide having concentrations up to and excess of 80% in one continuous cycle. The hydrogen peroxide production system can be set-up and installed using simple and cost-effective components. In addition, the production system and unit may be modular, compact, portable, simple to operate, and require minimal maintenance.

In another aspect of the present disclosure described herein, an enzymatic method and process for the continual manufacturing of hydrogen peroxide at room temperature in a single, on-site or stand-alone reactor or production chamber is provided. Here, the method can include NAD(P)H: quinone oxidoreductase 1 (NQO1) mediated reduction of a single working solution having at least one NQO1-activated compound (NAC) to generate an unstable semiquinone intermediately that spontaneously re-generates the parent NAC and simultaneously generates hydrogen peroxide. In addition, a working solution is provided a working solution is provided that contains excess reduced nicotinamide adenine dinucleotide (NADH), allowing the reaction to persist indefinitely while the parent NAC continuously regenerates. Further, the method can be processed within a molecular weight-specific semipermeable dialysis membrane that allows the diffusion of hydrogen peroxide there through while preventing the constituents of the working solution to pass through. In addition, the resulting hydrogen peroxide can be collected in an aqueous solution at a collection chamber. The collected hydrogen peroxide solution can be continuously pumped through and over the membrane, thereby creating an increasingly concentrated hydrogen peroxide solution exceeding 80% wt hydrogen peroxide per reaction membrane in a 12 hour run-time production cycle.

In another aspect of the disclosure described herein, the membrane, pump, and collection chamber can be housed together as one production unit. The production unit may also be modular in design wherein any number of production chambers, membranes, collection chambers, valves, and components in any configuration. In addition, the production unit may operate at room temperature with minimal energy requirements to operate the pump. Further, the hydrogen peroxide production method and system may operate with a production capacity of up to 20 kilo tons of hydrogen peroxide solution per year. In addition, the production method can be configured to operate continuously with NADH with a production capacity of hydrogen peroxide in the range of 2 to 15 ktpa capacity.

In another aspect of the disclosure described herein, a method of manufacturing hydrogen peroxide is provided.

The method can include mixing NQO1 enzyme, an NQO1 activated compound or molecule, and an NADH or NADPH cofactor with an aqueous solution, dispensing the aqueous solution within or onto a semi-permeable membrane, wherein the semi-permeable membrane further including a pre-defined molecular weight barrier. The method further includes wherein an oxidation-reduction reaction of the NQO1 enzyme, the NQO1 activated compound or molecule, and the NADH or NADPH cofactor within the aqueous solution produce hydrogen peroxide at a concentration level, and wherein the produced hydrogen peroxide is above the pre-defined molecular weight barrier of the semi-permeable membrane, and diffuses through the semi-permeable membrane. The method can further include extracting the produced hydrogen peroxide for retrieval at a collection chamber. The method can also include circulating the produced hydrogen peroxide through the membrane to produce a second concentration level of the hydrogen peroxide. In addition, the method can include dispensing one or more additional NQO1 enzyme, NQO1 activated compound, and NAD(P)H (or NADH cofactor or NADPH cofactor) into the aqueous solution. Here, the NQO1 activated compound can include one or more of: quinones, β-lapachone, streptonigrin, deoxynyboquinone, isobutyl-deoxynyboquinone, mitomycin C, KP372-1, phenothiazinium compounds, 2,5-diaziridinyl-3-(hydroxymethyl)-6-methyl-1,4-benzoquinone (RH1), apaziquinone (E09), indolquinones, pronoqodine A, quinolinoquinones, binaphtoquinones; and possibly Anthraquinone, Plastoquinone, Pyrroloquinoline quinone, Carbazilquinone, Chloranil, Dibromothymoquinone, Plastoquinone, Ubiquinone, Indolequinones, Porfiromycin, Pyrroliminoquinones, Atovaquone, Vitamin K, Vitamin K 1, Vitamin K 2, Vitamin K 3, and Atovaquone. Futher, the aqueous solution can include $H_2O$ and Tris-HCl. Here, the concentration level of the produced hydrogen peroxide can be 30% or more. In addition, the oxidation-reduction reaction can be a continuous cycle with 90% or more efficiency having 10% or less loss of the original NQO1 enzyme, NQO1 activated compound or molecule, and NADH or NADPH cofactors.

In another aspect of the disclosure described herein, a hydrogen peroxide production system is provided. The system can include an aqueous solution comprised of an NQO1 enzyme, an NQO1 activated compound or molecule, and an NADH or NADPH cofactor for producing hydrogen peroxide. The system further includes a production chamber having a semi-permeable membrane for receiving the aqueous solution. The membrane can further include one or more molecular weight barriers configured to diffuse the produced hydrogen peroxide there through. The system can also include a collection chamber for retrieving the produced hydrogen peroxide, and one or more pumps for circulating the aqueous solution having the hydrogen peroxide to the collection chamber and back to the production chamber. Here, the molecular weight barrier can be at least 100 Daltons. In addition, the system may also include a testing chamber for testing the produced hydrogen peroxide concentration levels. Further, the semi-permeable membrane can also have a tubular configuration. Also, the semi-permeable membrane can be at least partially suspended within the production chamber. Here, the system may further include a plurality of semi-permeable membranes. The system can also include a plurality of production chambers configured in parallel or series configurations. In addition, the production chamber, collection chamber, and pump can be portable and modular units or assembled as one portable and mobile unit.

In another aspect of the disclosure described herein, a method of manufacturing hydrogen peroxide is provided. Here, the method can include mixing one or more NQO1 enzymes, one or more NQO1 activated compounds, and a third substance. Here, the mixing can result in an oxidation-reduction reaction thereby producing hydrogen peroxide in a continuous cycle. Further, the third substance can be an NADH or NADPH cofactor. Alternatively, the third substance can also be hydrogen ($H_2$) gas and a platinum or palladium (Pd) catalyst.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which.

DETAILED DESCRIPTION

In the Brief Summary of the present disclosure above and in the Detailed Description of the Disclosure described herein, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

Figure 1A:
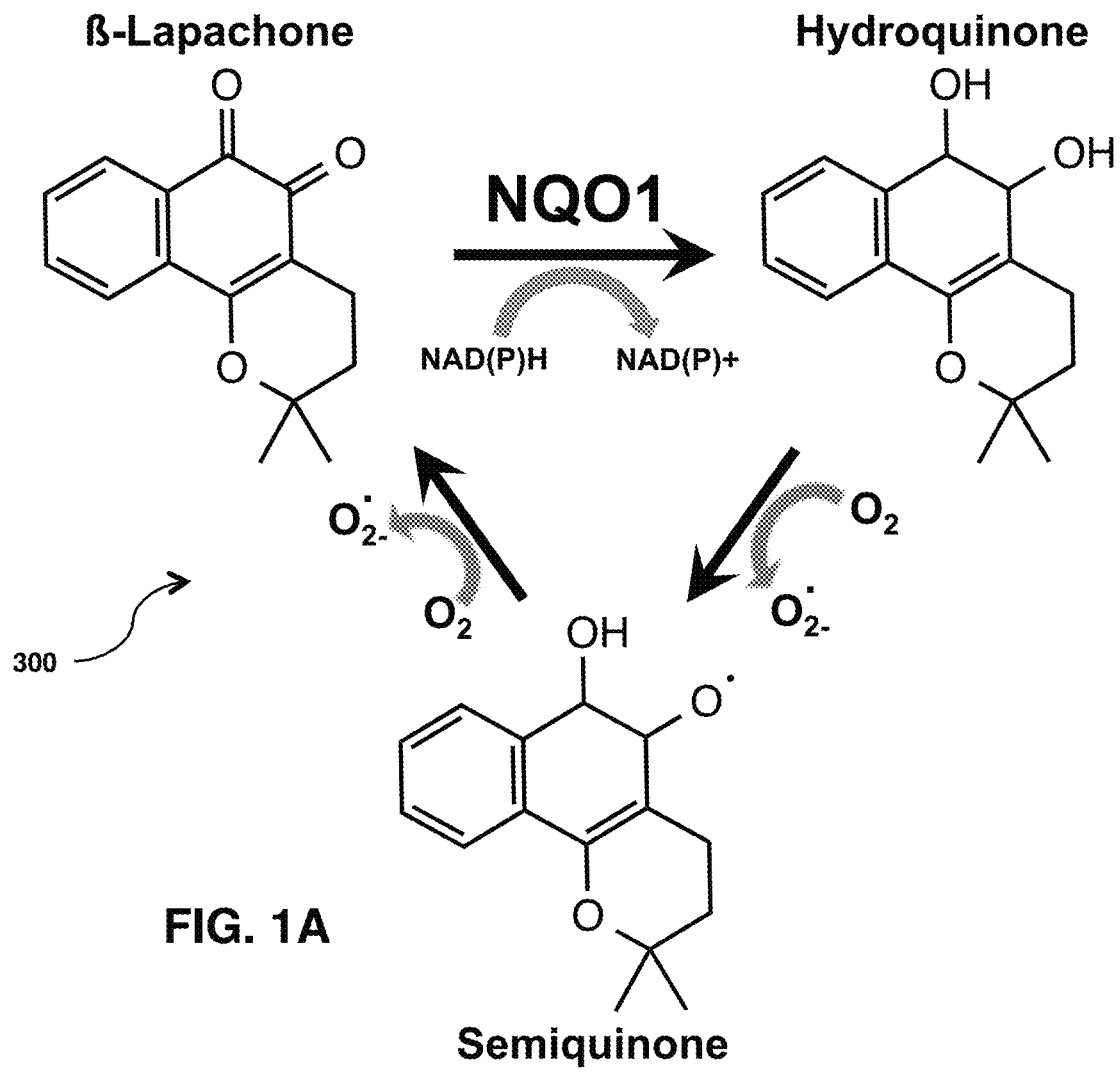
FIG. 1A illustrates a diagram for one non-limiting embodiment of a chemical reaction for the hydrogen peroxide production system and method of the disclosure described herein.
Figure 1B:
FIG. 1B illustrates a chemical reaction equation for the embodiment of FIG. 3A.

FIGS. 1A-1B, illustrate one embodiment for the hydrogen peroxide production method and system of the present disclosure described herein using an oxidation-reduction reaction. Here, the production method can use raw source material, solution, substances, molecules, or compositions that can include one or more of NQO1 activated compounds (NACs), NQO1, NADH or NADPH. Here, NADPH or NADH may also be represented as NAD(P)H. In general, NQO1 is a two-electron oxidoreductase enzyme found in living, biological systems that can utilize the hydrogen atoms from NADPH or NADH co-factors to hydrogenate quinones to a stable hydroquinone intermediate. However, a unique class of quinones or compounds exist, NQO1 activated compounds (NACs), that upon hydrogenation, form an unstable hydroquinone that spontaneously regenerates the parent quinone or compounds and produces hydrogen peroxide in the process. NADH is generally known as nicotinamide-adenine-dinucleotide in its reduced form and NADPH is generally known as nicotinamide-adenine-dinucleotide-phosphate in its reduced form. The NADH and NADPH substances are cofactors for a variety of enzymes, the majority of which catalyze oxidation-reduction reactions, such as NQO1. Here, the NQO1 enzyme operates as a catalyst by removing two hydrogen atoms from the NADPH or NADH cofactors and adds these hydrogen molecules to one or more NACs which then results in an un-stable hydroquinone, as shown in FIG. 1A. In the process, NADPH is oxidized thus reducing to $NADP^+$. Similarly, NADH can also be oxidized thus reducing to $NAD^+$.

Still referring to FIG. 1A-1B, a more detailed description of the hydrogen peroxide production method and system embodiment will now be described. In this embodiment, an NAC such as β-Lacaphone is mixed into a working solution in combination with NQO1 and NAD(P)H. Here, the NQO1 oxidizes the NAD(P)H to $NAD(P)^+$ by removing hydrogen atoms from the NAD(P)H and adding the hydrogen atoms to the β-Lacaphone quinone compound. This oxidation-reduction process then results in one or more hydroquinones, which are generally extremely un-stable molecules. From here, the chemical reaction proceeds wherein oxygen from an atmospheric environment donates an electron to the hydroquinones. Here, oxygen ($O_2$) becomes a superoxide anion radical ($O_2^-$) which then produces one or more un-stable semiquinones. The superoxide radical ($O_2^-$) then spontaneously reacts with water ($H_2O$), wherein the superoxide radical reacts with a proton donated from water and is converted to hydrogen peroxide ($H_2O_2$) and oxygen ($O_2$). Further, the semiquione then accepts or receives an electron from oxygen ($O_2$) molecule, generating another superoxide radical ($O_2^-$) which then forms hydrogen peroxide ($H_2O_2$, and regenerates the β-Lacaphone parent quinone compound in a continuous cycle fueled by NAD(P)H. The resulting hydrogen peroxide can then be extracted from the working solution.

Here, it is contemplated within the scope of the disclosure described herein that there may be any other type of NAC's or quinones may be used in the working or raw solution in addition to or in lieu of the β-Lacaphone. These NAC's may also be naturally occurring or man-made using non-natural synthetic processes. Here, NAC's that can be used within the system and process of the disclosure described herein can include but are not limited to: β-lapachone, streptonigrin, deoxynyboquinone, isobutyl-deoxynyboquinone, mitomycin C, KP372-1, phenothiazinium compounds, 2,5-diaziridinyl-3-(hydroxymethyl)-6-methyl-1,4-benzoquinone (RH1), apaziquinone (EO9), indolquinones, pronoqodine A, quinolinoquinones, binaphtoquinones; and possibly Anthraquinone, Plastoquinone, Pyrroloquinoline quinone, Carbazilquinone, Chloranil, Dibromothymoquinone, Plastoquinone, Ubiquinone, Indolequinones, Porfiromycin, Pyrroliminoquinones, Atovaquone, Vitamin K, Vitamin K 1, Vitamin K 2, Vitamin K 3, and Atovaquone, among others.

Figure 1C:
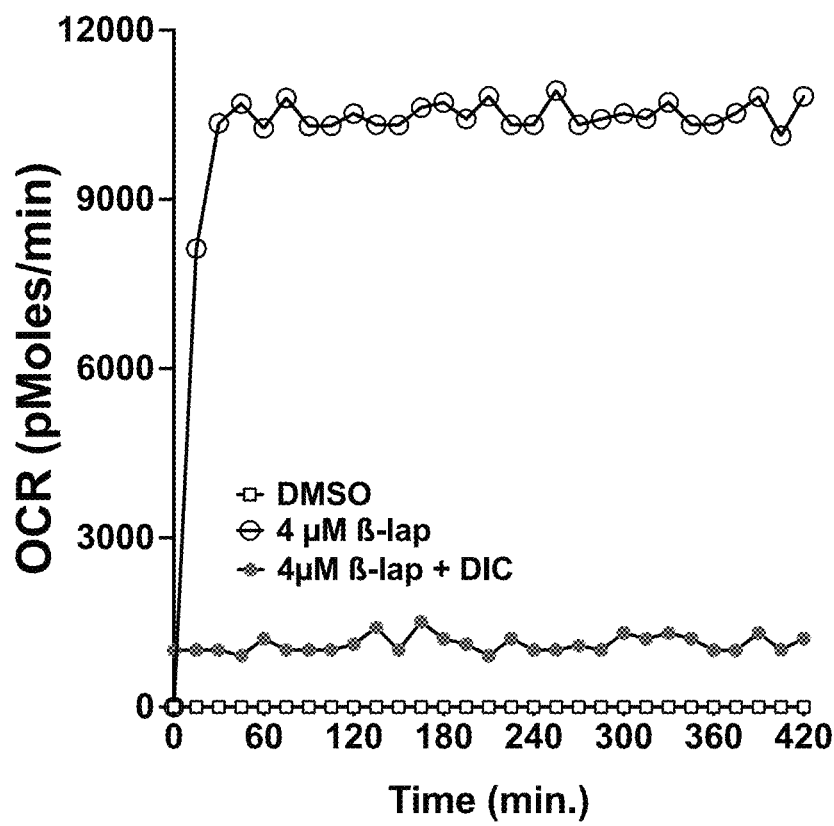
FIG. 1C-1D illustrate data charts of sample experiment data for one exemplary testing of hydrogen peroxide produced using the hydrogen peroxide production system and method of the disclosure described herein.
Figure 1D:
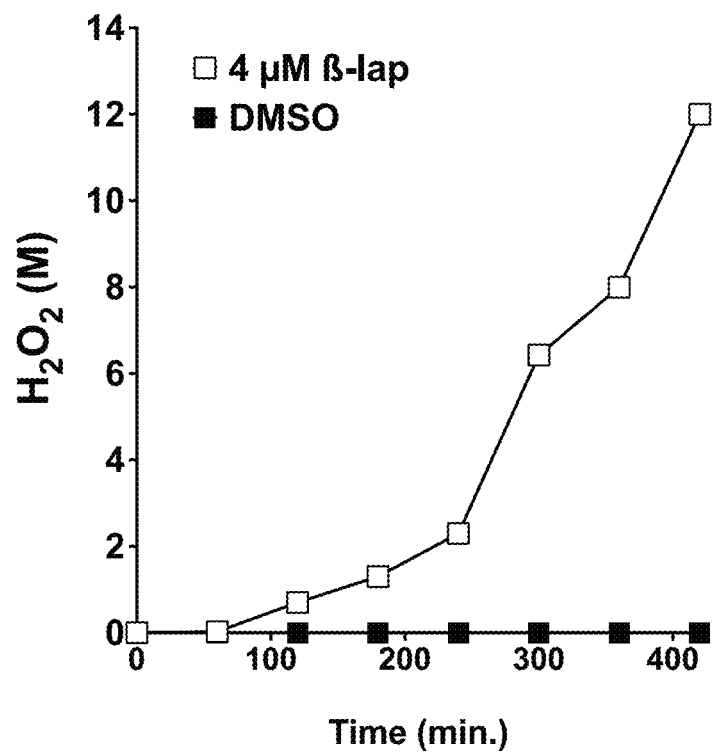

Referring now to FIG. 1C-1D, data graphs are provided illustrating the results of one sample experiment for hydrogen peroxide produced using the one or more embodiments of the present disclosure described herein. In particular, FIG. 1C illustrates the generation of superoxide radicals by using the Oxygen Consumption Rate (OCR) with respect to time as a proxy for one experiment. Here, the experiment comprised using a Seahorse Bioscience XF Analyzer® instrument to measure the OCR with respect to time. In addition, a 96-well plate was used wherein each well was filled with 140 microliters of 100 units of NQO1, NADH, 4 micromolar NAC (β-Lacaphone), 50 millimolar Tris-HCl at pH 7 wherein the solutions were kept at atmospheric temperature. Here, each well had an optical sensor for measuring the oxygen content thereby providing an effective OCR with respect to time. During a 7-hour period, wherein the wells were measured every 2-minute interval, it was observed that the OCR in the wells incubated with β-lapachone dramatically increased and sustained OCR, while control wells treated with the vehicle dimethyl sulfoxide (DMSO) did not change baseline OCR levels (FIG. 1C), thereby indicating that the NQO1 enzyme is continuously consuming oxygen and converting oxygen to a super-oxide radical ($O_2$). Further, at the conclusion of this 7-hour period, approximately 12 molar hydrogen peroxide was produced and measured. Hence, for a 7-hour run cycle, the resulting hydrogen peroxide concentration was measured to be in excess of 30%. Specifically, referring to FIG. 1D, the hydrogen peroxide concentration was measured using a spectrophotometric absorption of 240 nm corresponding to hydrogen peroxide.

Figure 1E:
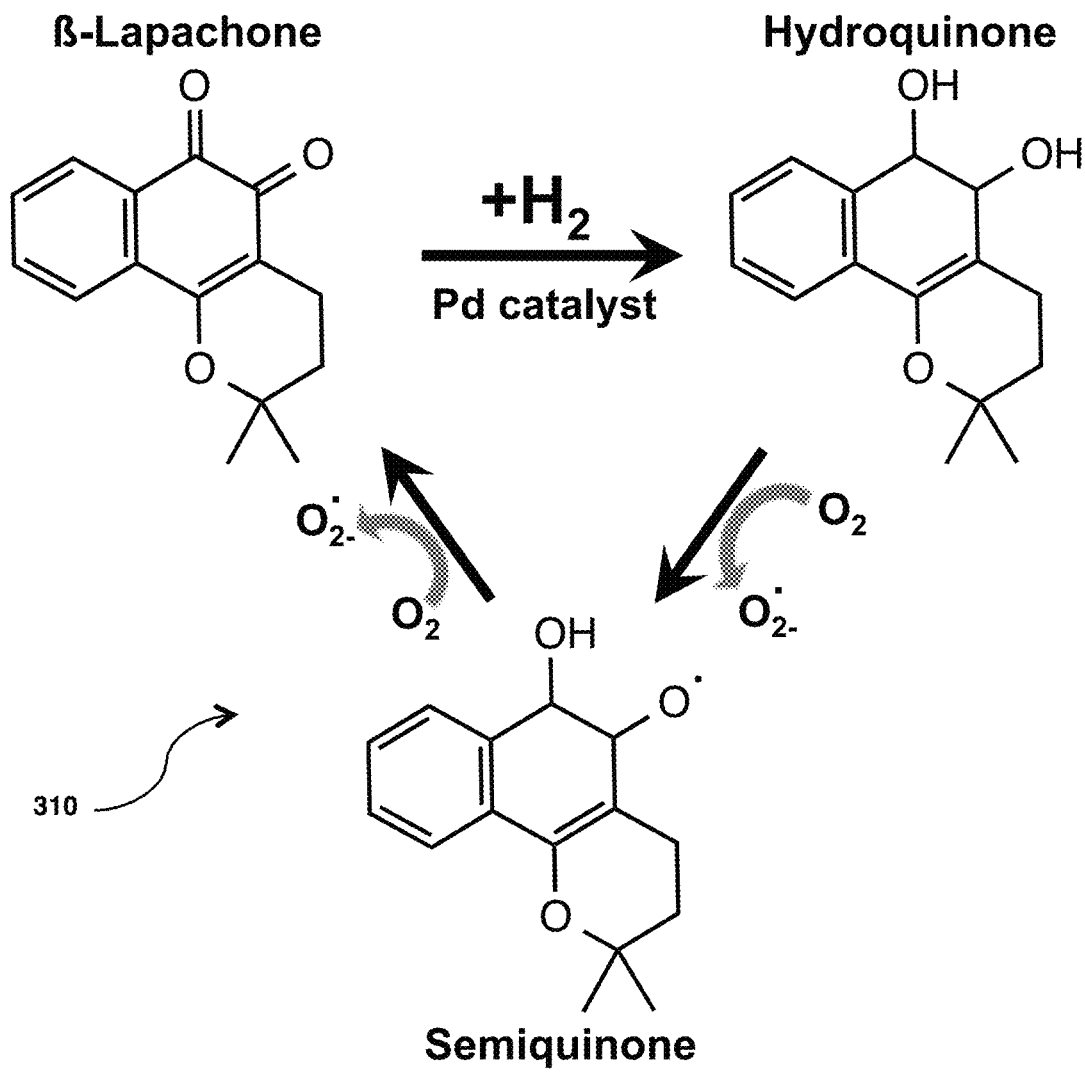
FIG. 1E illustrates another non-limiting embodiment of a diagram for a hydrogen peroxide production system and method of the disclosure described herein.

FIG. 1E illustrates another embodiment for a hydrogen peroxide production method and system of the present disclosure described herein. In this embodiment, an NAC such as β-Lacaphone is used in a working solution 310 in combination with hydrogen ($H_2$) gas and platinum or palladium (Pd) to produce hydrogen peroxide without the use of NQO1 or NADH/NADPH. Here, the palladium (Pd) operates as a catalyst by using hydrogen gas bubbled through the apparatus to hydrogenate both ketones present in β-lapachone to the hydroquinone form. This oxidation-reduction process then results in one or more unstable hydroquinones. From here, the chemical reaction proceeds wherein oxygen from an atmospheric environment donates an electron to the hydroquinones. Here, oxygen ($O_2$) becomes a superoxide anion radical ($O_2^-$) which then produces one or more un-stable semiquinones. The superoxide radical ($O_2^-$) then spontaneously reacts with water ($H_2O$), wherein the superoxide radical then gets converted to hydrogen peroxide ($H_2O_2$). Further, the semiquione then accepts or receives an electron from an oxygen ($O_2$) molecule thereby re-making the β-Lacaphone quinone compound and further generating superoxide radical/hydrogen peroxide in a continuous cycle limited only by the amount of $H_2$ gas available. The resulting hydrogen peroxide can then be extracted from the working solution.

Figure 2A:
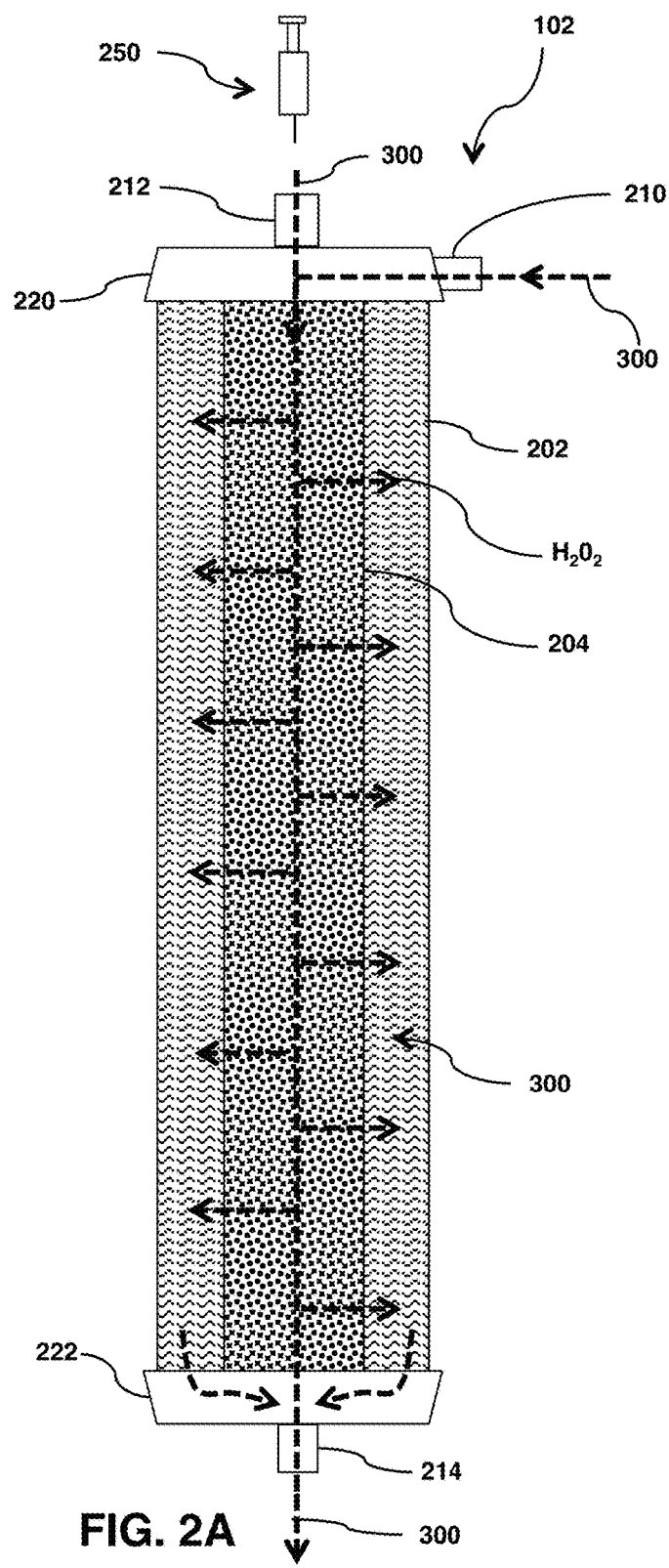
FIG. 2A illustrates a cross-sectional side view of one non-limiting embodiment for a hydrogen peroxide production chamber of the disclosure described herein.
Figure 2B:
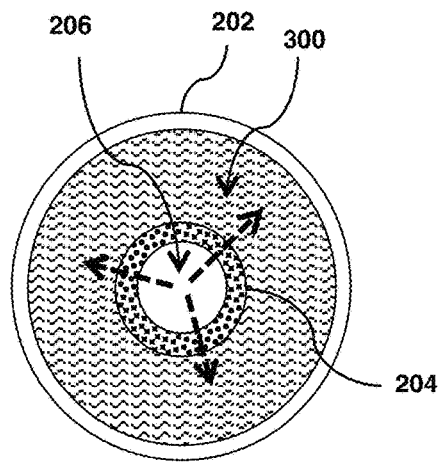
FIG. 2B illustrates a cross-sectional top view of one non-limiting embodiment for the hydrogen peroxide production chamber of the disclosure described herein.
Figure 2C:
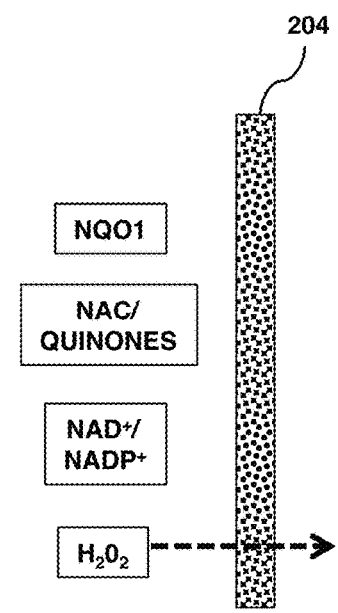
FIG. 2C illustrates a partial cross sectional side view of a semi-permeable membrane of the production chamber.

FIG. 2A-2C illustrate one embodiment for a production chamber of the hydrogen peroxide production system and method of the present disclosure described herein. In particular, the production chamber 102 can include a tubular housing 202 that further houses a tubular dialysis membrane 204. In addition, housing 202 further includes end caps 220 and 220, for receiving and sending a working solution 300. In particular, end cap 220 includes an inlet port 210 for receiving the circulating working solution 300 and an inlet injection port 212 for receiving one or more raw or source materials, substances, or compounds of the working solution 300, such as raw or source materials NQO1, Hydrogen ($H_2$), NAC/quinones, and NADH/NADPH, among others. Here, an injection syringe needle 250 is shown for injecting the source materials for the working solution 300 into the inlet injection port 212, however, it is contemplated within the scope of the invention than any other injection or dispensing apparatus or system may be used for injecting or dispensing the working solution 300 or source materials for the working solution to and within membrane 204 and housing 202. In one embodiment, the injected and circulating working solution can travel through inlets 210 and 212 and directly within the interior space 206 of tubular membrane 204. Here, membrane 204 can either be suspended or freely floating within housing 202, or in the alternative, membrane 204 can be coupled or fixed to housing 202.

Still referring to FIG. 2A-2C, membrane 204 can have a specified or pre-determined molecular weight barrier cut-off. More specifically, any substance, compound, solution, or molecules within the interior chamber space 206 of membrane 204 that are larger in molecular weight than the specified or pre-determined cut-off will be trapped within space 206 of membrane 204. In contrast, any substance, compound, solution, or molecules that are less than the pre-determined cut-off will diffuse through the membrane. In the current embodiment, membrane 204 is made of a semi-permeable material that can have a pre-defined 100 Dalton molecular weight cut-off, however, it is contemplated within the scope of the invention that any suitable molecular weight cut-off may also be used, including but not limited to 50 Daltons through 150,000 Daltons. Here, the NQO1 and NAC/quinones of the present disclosure described herein have a molecular weight that is larger than the specified cut-off for the membrane (i.e. larger than 100 Daltons), hence, the NQO1, NAC/quinones, and $NAD^+$/$NADP^+$ of the working solution 300 are trapped within membrane 204 and do not diffuse through. As previously discussed within this disclosure, the resulting byproduct of the NQO1, NAC/quinones, and NAD/NADP reaction is hydrogen peroxide, wherein hydrogen peroxide has a molecular weight that is less than the pre-determined or specified molecular weight of membrane 204 (i.e. less than 100 Daltons). Hence, hydrogen peroxide will subsequently diffuse through membrane 204 and out to the interior space of housing 202, wherein the resulting working solution 300 (which now includes the hydrogen peroxide concentration), is pumped out of the housing through outlet 214 and to one or more collection chambers or for additional processing and circulation.

Still referring to FIGS. 2A-2C, the previously discussed process proceeds in a continuous cycle until a pumping operation is ceased. More specifically, as the working solution 300 exits outlet 214, it is eventually re-circulated by being pumped back through inlet 210, where it again enters interior space 206 of membrane 204 to produce additional hydrogen peroxide molecules. It is contemplated within the scope of the disclosure described herein that through each re-circulation or iteration of the working solution 300, the hydrogen peroxide concentration of the working solution 300 increases. It is further contemplated within the scope of the disclosure described herein that no additional raw source materials or substances are needed after an initial injection thereof to reach a threshold or pre-defined hydrogen peroxide concentration. However, in other embodiments, depending on the application, volume, quantity, use, and concentrations desired, one or more raw source materials may be periodically, intermittently, or continuously injected or dispensed within one or more of membrane 204, housing 202, and production chamber 102. In addition, it is contemplated within the scope of the disclosure described herein that the initial working solution 300 (or the raw source materials), prior to producing hydrogen peroxide, can be comprised of a buffering agent/substance/compound, spring or distilled water, ethylene, Tris, or Tris-Hydrochloride (Tris-HCl), among others. For example, referring to FIG. 3, in one embodiment, the initial working solution 300 having the buffering agent or Tris-HCl may be within storage chamber 108 or collection chamber 104, wherein the initial working solution 300 is pumped out of either chamber 108 or 104 and into production chamber 102, thereby adding, producing, and increasing the hydrogen peroxide concentration of the working solution 300.

Figure 3:
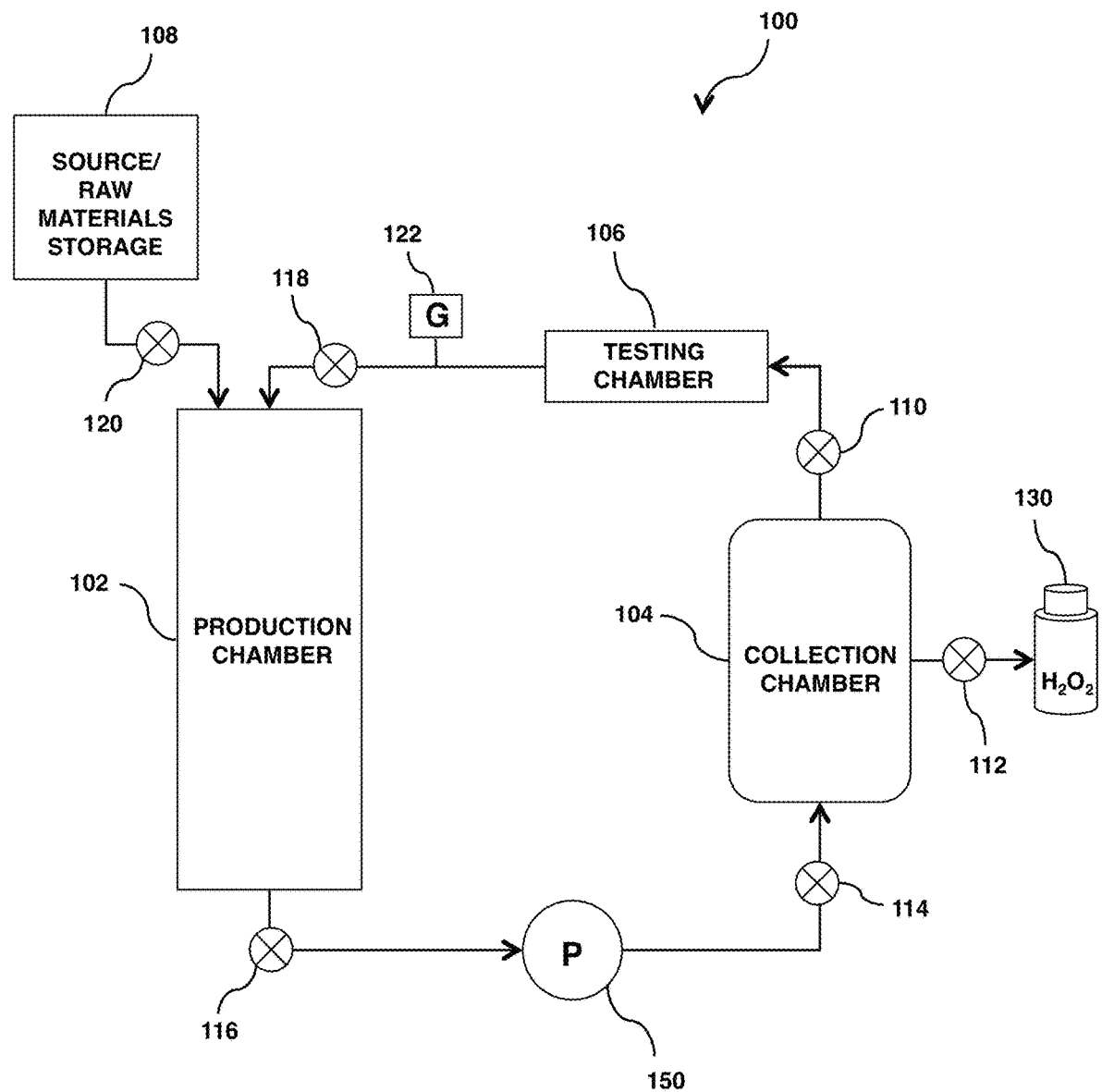
FIG. 3 illustrates a schematic diagram for one non-limiting embodiment of the hydrogen peroxide production system and method of the disclosure described herein.

FIG. 3 illustrates one non-limiting embodiment for a hydrogen peroxide production method, system, and apparatus 100 of the disclosure described herein. More specifically, in this embodiment, the hydrogen peroxide production system 100 can be a closed-loop system that can include a production chamber 102 that receives source, raw, or working solutions 300 from a storage source 108. The system further includes one or more peristaltic pumps 150 for circulating and re-circulating the working solution and the $H_2O_2$ solution within the system. However, it is contemplated within the scope of the disclosure described herein that any type of fluid or positive displacement pump may be used. In addition, the system includes a collection chamber 104 for receiving, storing, collecting, and dispensing the $H_2O_2$ to a batch or packaging 130. Alternatively, the collection chamber may also store the initial working solution prior to commencing a cycle, with or without a hydrogen peroxide concentration. The system can further include a testing chamber 106 for simultaneously or periodically testing the concentration and purity of the working solution or $H_2O_2$ circulating through the system, and one or more gauge readouts 122 for detecting the flow rate, pressures, temperatures, and other thermodynamic or chemical properties of the system and $H_2O_2$ circulating within the system. The production system 100 can further include a plurality of valves 110, 112, 114, 116, 118, and 120 for controlling the flow rate, bypass, shut-off, or isolation of one or more units, components, and chambers within the production system. It is contemplated within the scope of the invention that any type of manual or automatic valve may be used within the production system, including but not limited to gate valves, one-way/two-way/three-way valves, butterfly valves, glob valves, piston valves, solenoid valves, and ball valves, among others. In addition, it is contemplated within the scope of the invention that chambers 102, 104, 106, and 108 may be of any size, dimension, or volumetric capacity.

Figure 4:
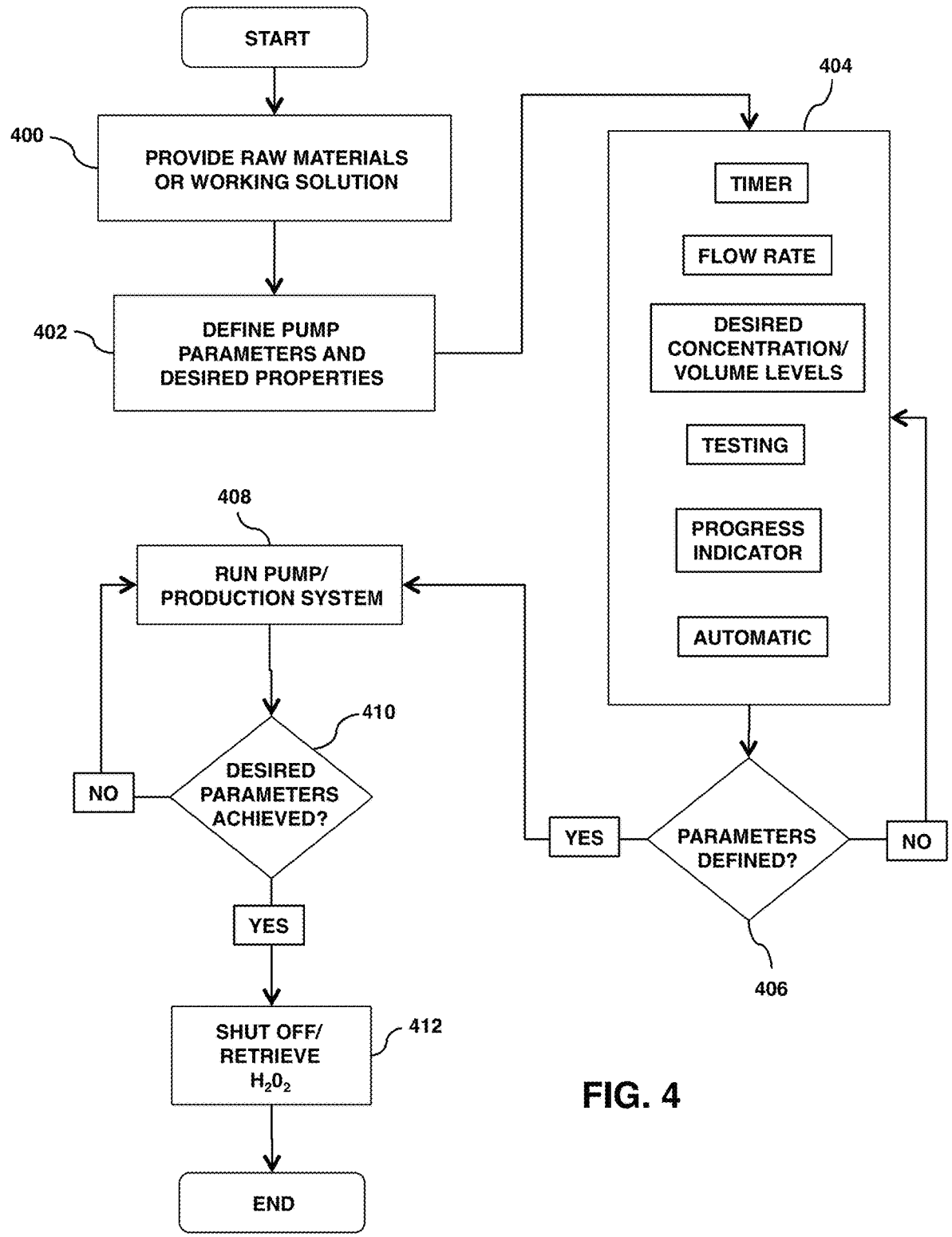
FIG. 4 illustrates a block diagram for one non-limiting embodiment for a process of producing hydrogen peroxide for the hydrogen peroxide production system and method of the disclosure described herein.

FIG. 4 illustrates one embodiment for a method of operation of the hydrogen peroxide production system and method of the disclosure described herein. In particular, the process can start at step 400, wherein raw source materials or initial working solution are introduced into the production chamber of the system. At step 402, one or more pumps within the system may be programmed or receive operational parameters for running one or more hydrogen production pumping cycles. Here, it is contemplated within the scope of the disclosure described herein that the pump may include one or more control units, controllers, microprocessors, memory, and storage units for executing one or more pre-programmed or user-defined operations, applications, logic, algorithms, software, and commands. More specifically, at step 404, a user may define or schedule a timed operation within a timer or scheduling module of the pump, such as start/stop times, day/month/year, daily, monthly, yearly, single-use, or periodic operations. In addition, the user may also define or set a constant or variable flow-rate for the pump operation. Further, user may also define or set a desired threshold hydrogen peroxide concentration or volume levels. More specifically, in such an embodiment, the pump may continue to operation and re-circulate the working solution within the system until a pre-defined or user-defined hydrogen peroxide concentration level is reached, and wherein the pump may shut-off automatically, or in the alternative, notify or alert one or more users. As such, the pump may also include a testing module for automatically, periodically, or continuously testing the hydrogen peroxide concentration levels of the working solution passing through the pump. Further, the pump may also include a progress indicator for indicating various factors, including but not limited to: current concentration levels, desired concentration levels, flow rate, estimated time remaining until completion of one or more production cycles, temperatures, environmental conditions, stable or un-stable conditions, and any notifications, alerts, or errors, among others. Also, the pump may include functionality for automatic, semi-automatic, or manual operation.

Still referring to FIG. 4, at step 406, once the parameters have been defined, the process can proceed to step 408. At step 408, the process can commence the hydrogen production cycle. It is contemplated within the scope of the invention that each cycle can operate continuously in operation from one (1) minute up to and including 365 days, depending on the intended application, use, volume, and desired hydrogen peroxide concentration levels. At step 410, once the one or more pre-defined or threshold parameters are reached, the process may then proceed to step 412, wherein the pump and production system may automatically shut-off, rest, or repeat the cycle after a pre-determined time. In addition, at this step, the working solution batch having the hydrogen peroxide composition may be extracted, removed, dispensed, or packaged for distribution. Alternatively, the working solution batch may be re-introduced back into the production system in full or in part for additional hydrogen peroxide production.

Figure 5:
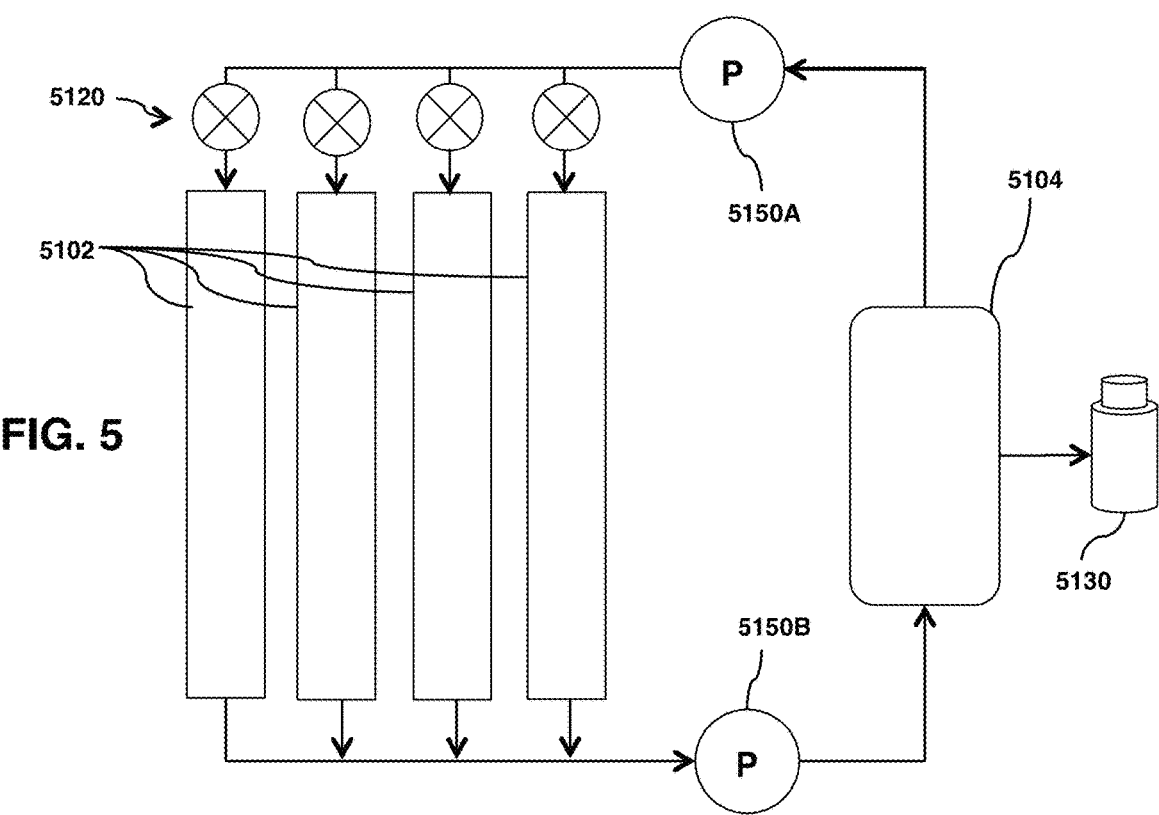
FIG. 5 illustrates a schematic diagram for another non-limiting embodiment of a production system for the hydrogen peroxide production system and method of the disclosure described herein.

FIG. 5 illustrates another embodiment for a hydrogen peroxide production system of the disclosure described herein. In this embodiment, the system may include a plurality of production chambers 5102 connected in parallel and a plurality of valves 5120 controlling the input to the chambers. One or more of the chambers 5102 may be operational at any given time depending on the intended use, application, volume, and hydrogen peroxide concentration desired. The system may also include a first pump 5150A and second pump 5150B in order to further provide additional flow rate and assure constant pump head pressure throughout the system for circulating the working solution. In addition, the system may include a collection chamber 5104, wherein the resulting hydrogen peroxide batch 5130 may be recovered. It is contemplated within the scope of the invention that any one or more valves or components may also be incorporated into the system of FIG. 5.

Figure 6:
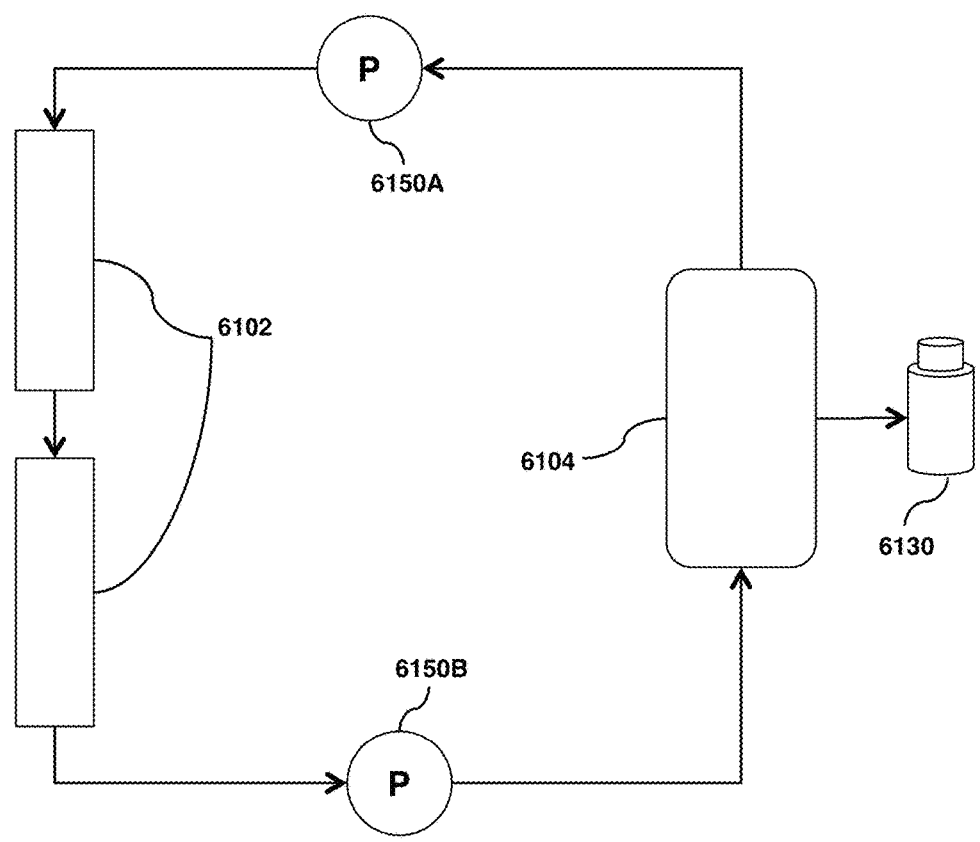
FIG. 6 illustrates a schematic diagram for another non-limiting embodiment of a production system for the hydrogen peroxide production system and method of the disclosure described herein.

FIG. 6 illustrates another embodiment for a hydrogen peroxide production system of the disclosure described herein. In this embodiment, the system may include a plurality of production chambers 6102 connected in a series configuration wherein a plurality of pumps 6150A and 6150B further circulate the working solution through a collection chamber 6104, wherein the working solution containing hydrogen peroxide batch 6130 may be recovered. Here, it is contemplated within the scope of the disclosure described herein that the addition of production chambers connected in series can further help amplify the hydrogen peroxide production chemical reaction within the production chambers. Also, the addition of additional production chambers can further help purify the working solution. It is contemplated within the scope of the invention that any one or more valves or components may also be incorporated into the system of FIG. 6.

Figure 7:
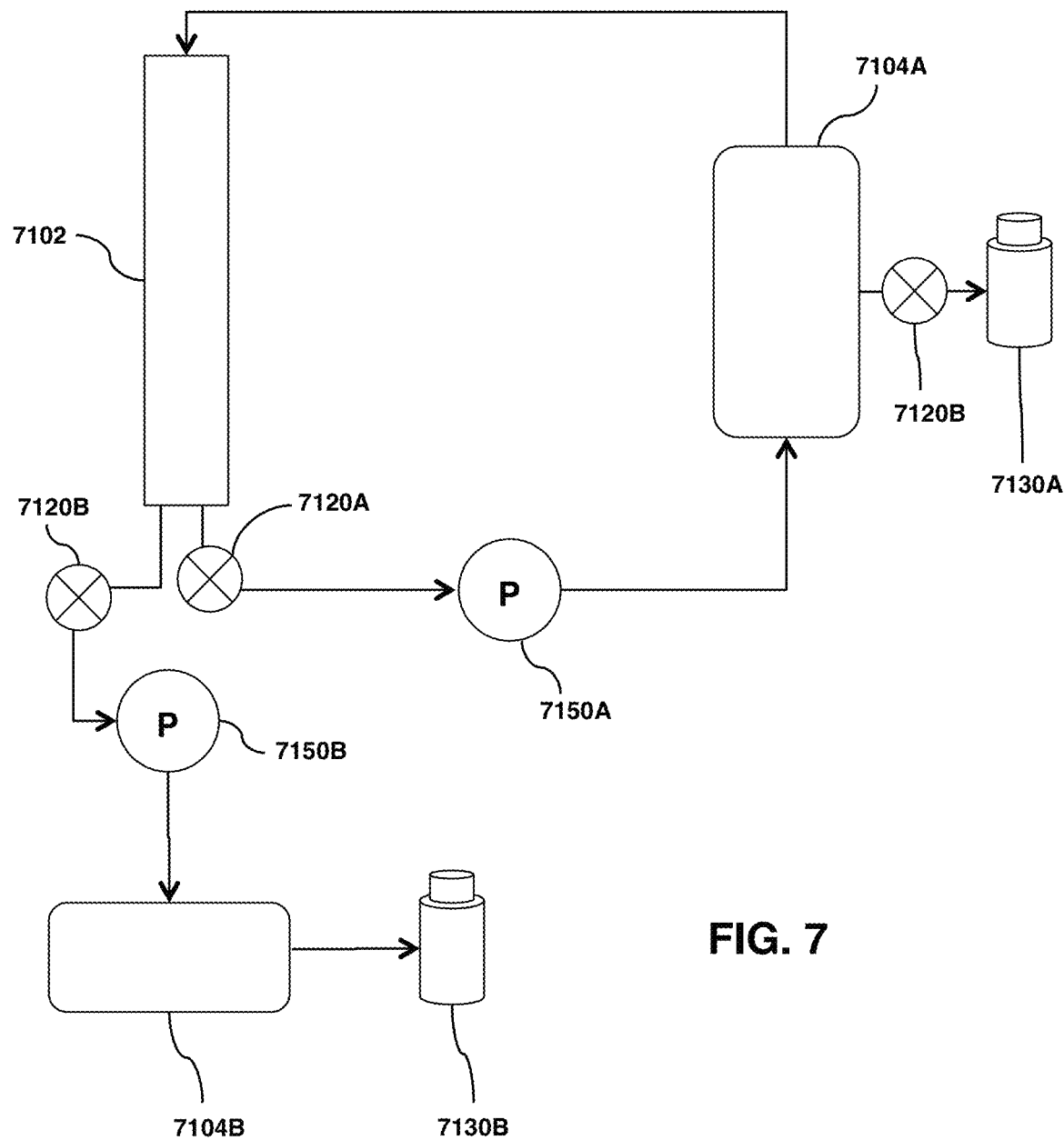
FIG. 7 illustrates a schematic diagram for another non-limiting embodiment of a production system for the hydrogen peroxide production system and method of the disclosure described herein.

FIG. 7 illustrates another embodiment for a hydrogen peroxide production system of the disclosure described herein. In this embodiment, the system may include a production chamber 7102 in communication with a first collection chamber 7104A and a second collection chamber 7104B. In this embodiment, pre-defined volume or percentage of the working solution may be diverted to collection chamber 7104B via opening of valve 7120B and operation of pump 7150B thereby directing the working solution to collection chamber 7104B to be later recovered as batch 7130B. The remaining working solution within the system may continue to circulate through pump 7150A, collection chamber 7104A and back through production chamber 7102.

It is contemplated within the scope of the invention that any one or more valves or components may also be incorporated into the system of FIG. 7.

Figure 8:
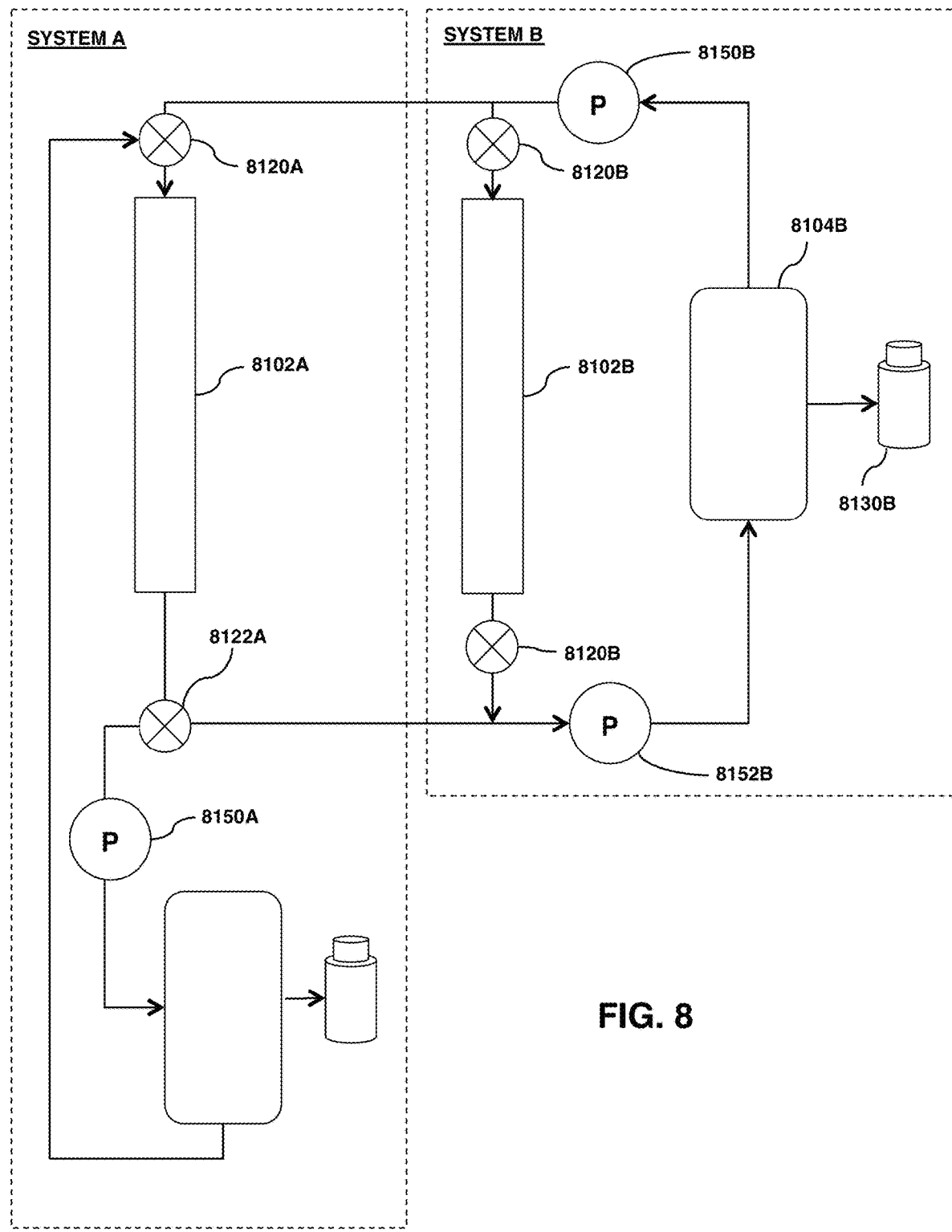
FIG. 8 illustrates a schematic diagram for another non-limiting embodiment of a production system for the hydrogen peroxide production system and method of the disclosure described herein.

FIG. 8 illustrates another embodiment for a hydrogen peroxide production system of the disclosure described herein. In this embodiment, the system may be a two-part system that can work in unison with each other or independent of each other. Here, system A may include a production chamber 8102A that may be isolated from system B by closing valves 8120A and 8122A. Such a two-part system may be used in a production system wherein two or more separate hydrogen peroxide concentration levels or volumes may be desired. Similarly, system B may be isolated from system A via closing of valves 8120B and 8122B. Each system can include its own independent pumping systems and collection chambers. It is contemplated within the scope of the invention that any one or more valves or components may also be incorporated into the system of FIG. 8.

Figure 9:
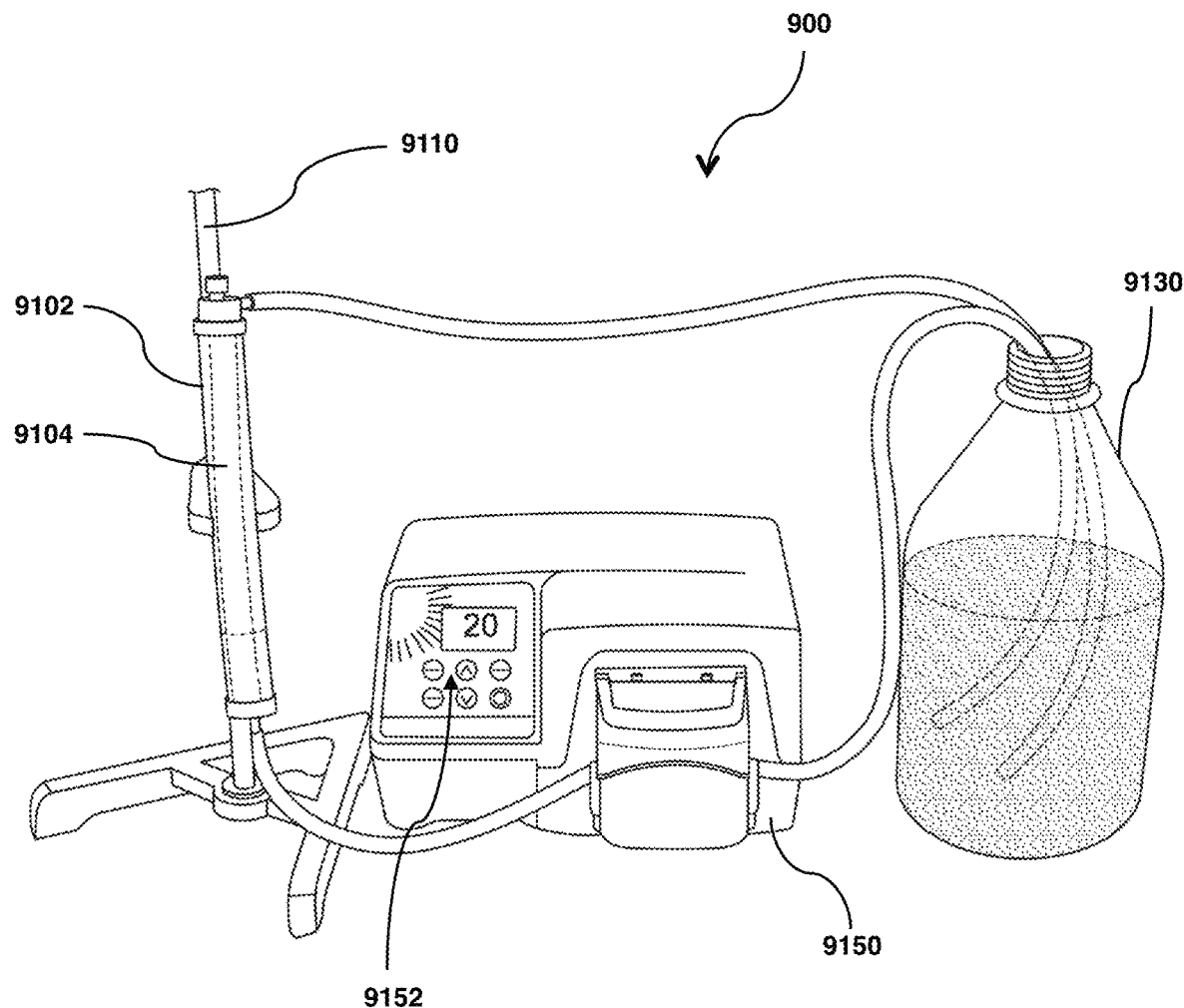
FIG. 9 illustrates a front elevated perspective view for one non-limiting embodiment of a portable hydrogen peroxide production apparatus of the disclosure described herein having modular components.

FIG. 9 illustrates one embodiment for a hydrogen peroxide production apparatus having modular components. In particular, the production apparatus 900 can include a tubular production chamber 9102 having a tubular semi-permeable membrane 9104 freely suspended or fixed therein. Here, production chamber 9102 may also be configured in an upright position and secured via a holder or stand 9110. The production chamber is in fluid communication pump 9150, wherein pump 9150 further include a user interface for 9152 for setting various parameters of the pump operation, including but not limited to a timed operation, hydrogen peroxide concentration desired level, on/off, flow rate, manual, automated, or pre-programmed operations and schedules, among others. Pump 9150 is also in fluid communication with collection chamber 9130, for circulating and pumping the aqueous solution from production 9102 to collection chamber 9130. In addition, collection chamber 9130 is also in fluid communication with production chamber 9102, wherein pump 9150 can pump and circulate the contents or aqueous solution of collection chamber 9130 to production chamber 9102. Here, it is contemplated within the scope of the disclosure herein that the pump may circulate the aqueous solution via any type of flexible or rigid tubing or piping.

Figure 10A:
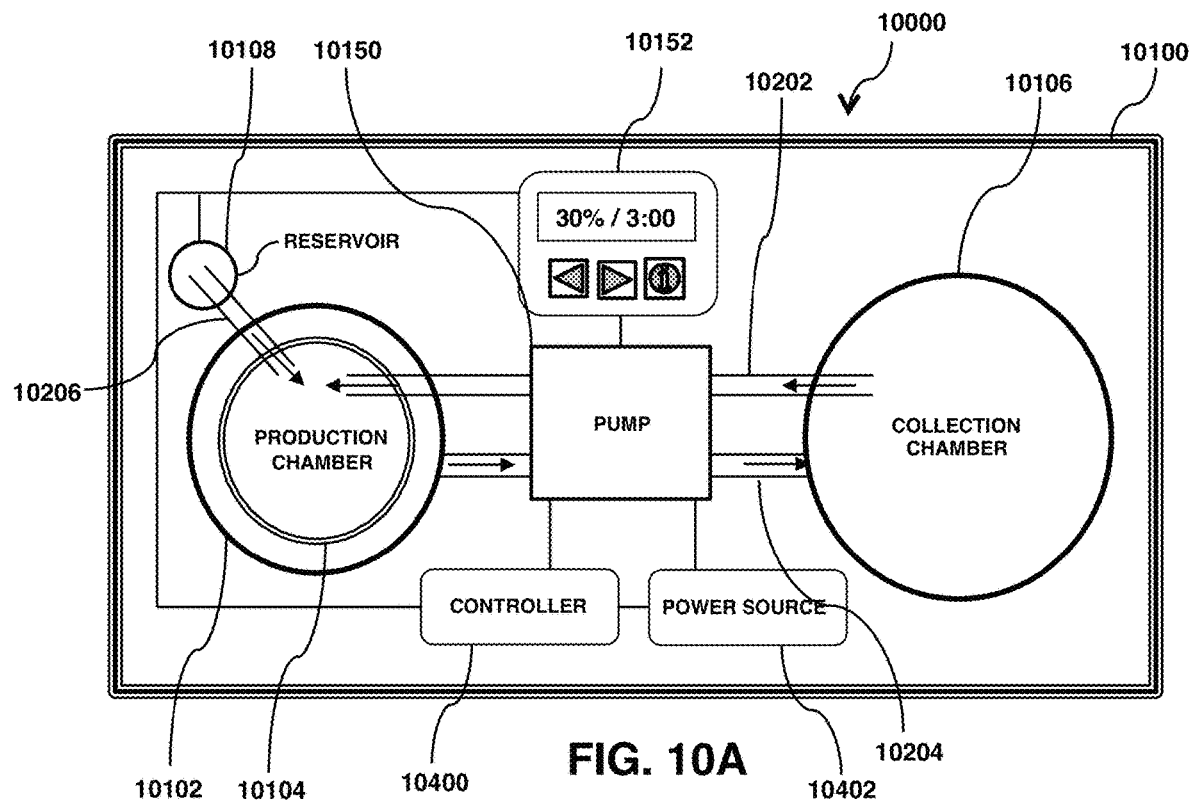
FIG. 10A illustrates a top view for one non-limiting embodiment of a portable hydrogen peroxide production apparatus of the disclosure described herein as one single-unit.
Figure 10B:
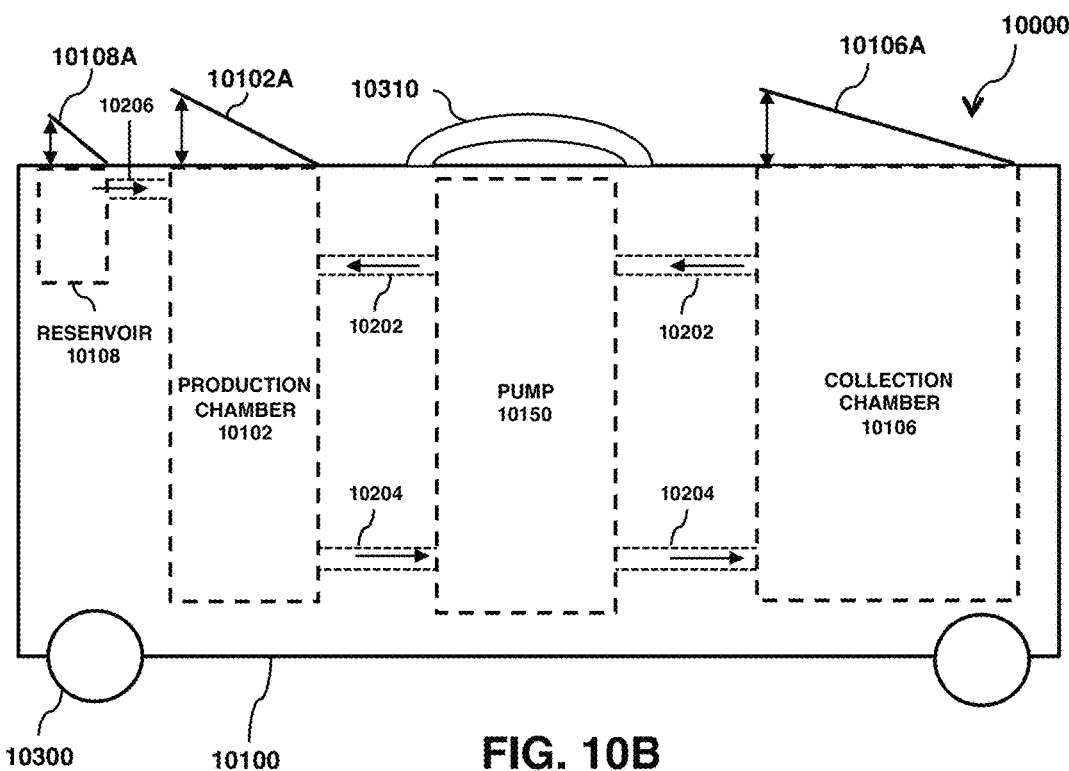
FIG. 10B illustrates a partial side view for the embodiment of FIG. 10A

FIG. 10A-10B illustrate another embodiment for the hydrogen peroxide production system and apparatus of the disclosure described herein configured as a single portable and mobile unit. FIG. 10A illustrates a top view of the portable unit 10000, wherein a top cover is removed, thereby illustrating some of the interior components. Specifically, unit 10000 can include a casing or housing 10100 for enclosing a production chamber 10102, semi-permeable membrane 10104 within the production chamber, collection chamber 10106, raw source reservoir 10108, pump 10150, user interface 10152, tubes 10202, 10204, and 10206, controller or control unit 10400, and a power source 10402, among others. However, it is contemplated within the scope of the disclosure described herein that any other parts, components, or control devices may also be included in combination or in lieu of the aforementioned components. Still referring to FIG. 10A, controller 10400 can include a microprocessor, memory, storage device, logic, software, application, algorithm, and programming stored thereon, among others, for controlling operation of the hydrogen peroxide production method, system, and apparatus of the disclosure described herein. Here, logic, software, application, algorithm, and programming may include any non-transitory computer readable medium storing thereon a program, which when executed by a computer, causes the computer to perform a method or function. Further, controller 10400 can further electrically communicate and send/receive commands with pump 10150, graphical user interface 10152, reservoir 10108, production chamber 10102, and collection chamber 10108. Here, tube 10204 is in fluid communication with production chamber 10102 wherein its contents are outputted to pump 10150 and collection chamber 10106. Tube 10202 is in fluid communication with collection chamber 10106 wherein its contents are outputted to pump 10150 and production chamber 10102.

FIG. 10B illustrates a side view of the portable hydrogen peroxide production unit 10000. In particular, unit 10000 can further include a plurality of wheels or casters 10300 for mobility. In addition, unit 10000 can also include a handle 10130 for additional portability and mobility. Further, housing 10100 can further include access and closure part 10106A for accessing chamber 10106, access and closure part 10102A for accessing production chamber 10102, and access and closure part 10108A for accessing reservoir 10108. Here, it is contemplated within the scope of the disclosure herein that any of parts 10102A, 10106A, and 10108A may be any hinge operated, pivoting, locking, or sliding access lid, cover, closure, or seal.

It is contemplated within the scope of the disclosure described herein that hydrogen peroxide concentration levels in excess of 80% may be produced using the one or more embodiment disclosed herein. In addition, any of the aforementioned production systems and methods with respect to FIGS. 1A-10B may be as part of a small to medium or medium to large-scale production plant. Alternatively, the productions systems of FIGS. 1A-10B may also be a portable or mobile hydrogen production system that can have individual modular components or be a part of one single unit.

From the foregoing it will be seen that the disclosure described herein is one well adapted to attain all ends and objectives herein-above set forth, together with the other advantages which are obvious and which are inherent to the disclosure described herein.

Since many possible embodiments may be made of the disclosure described herein without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the disclosure described herein is not limited to the specific forms or arrangement of parts described herein, except insofar as such limitations are included in the following claims. Further, it will be understood that certain features and sub-combinations are of utility and may be employed without reference to other features and sub-combinations.

What is claimed is:

1. A hydrogen peroxide production system, the system comprising:
    an aqueous solution comprised of an NAD(P)H:quinone oxidoreductase 1 (NQO1) enzyme, an NQO1 activated compound or molecule, and an NADH or NADPH cofactor for producing hydrogen peroxide;
    a production chamber having a semi-permeable membrane for receiving the aqueous solution;
    the membrane further comprising one or more molecular weight barriers configured to diffuse the produced hydrogen peroxide there through;
    a collection chamber for receiving the produced hydrogen peroxide; and one or more pumps for circulating the aqueous solution having the hydrogen peroxide to the collection chamber and back to the production chamber.

2. The system of claim 1, wherein the molecular weight barrier is further comprised of at least a 100 Daltons cut-off.

3. The system of claim 1, further comprising a testing chamber for testing the produced hydrogen peroxide concentration levels.

4. The system of claim 1, wherein the semi-permeable membrane further comprises a tubular configuration.

5. The system of claim 1, wherein the semi-permeable membrane is at least partially suspended within the production chamber.

6. The system of claim 1, further comprising a plurality of semi-permeable membranes.

7. The system of claim 1, further comprising a plurality of production chambers configured in parallel or series configurations.

8. The system of claim 1, wherein the production chamber, collection chamber, and pump are portable units.

* * * * *